United States Patent

Maurer et al.

[11] Patent Number: 4,542,126
[45] Date of Patent: Sep. 17, 1985

[54] PESTICIDALLY ACTIVE PYRIMIDIN-5-YL-(THIO)PHOSPHORIC ACID ESTER-AMIDES

[75] Inventors: Fritz Maurer, Wuppertal; Bernhard Homeyer, Leverkusen; Benedikt Becker, Mettmann; Gerd Hänssler, Leverkusen, all of Fed. Rep. of Germany

[73] Assignee: Bayer Aktiengesellschaft, Leverkusen, Fed. Rep. of Germany

[21] Appl. No.: 585,322

[22] Filed: Mar. 1, 1984

[30] Foreign Application Priority Data

Mar. 15, 1983 [DE] Fed. Rep. of Germany ....... 3309124

[51] Int. Cl.[4] .......................... A01N 57/32; C07F 9/65
[52] U.S. Cl. ......................................... 514/86; 544/243
[58] Field of Search ......................... 544/243; 424/200

[56] References Cited
U.S. PATENT DOCUMENTS 3,169,973 2/1965 Szabo ............................... 424/200 X
3,716,600 2/1973 Magee ................................. 260/959
4,486,422 12/1984 Costales et al. ..................... 424/200

Primary Examiner—Donald G. Daus
Assistant Examiner—Diana G. Rivers
Attorney, Agent, or Firm—Sprung, Horn, Kramer & Woods

[57] ABSTRACT

Pyrimidin-5-yl-(thio)phosphoric acid ester-amides of the formula

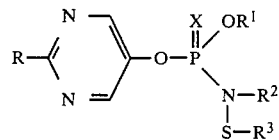

in which
X is oxygen or sulphur,
R is hydrogen, alkyl, aryl or cycloalkyl,
$R^3$ is alkyl, halogenoalkyl, cyanoalkyl, mono- or di-alkylamino, optionally substituted aryl, or

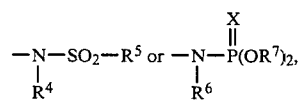

$R^1$, $R^2$, $R^4$, $R^6$ and $R^7$ each independently is alkyl, and
$R^5$ is alkyl or optionally substituted aryl which possess pesticidal activity.

12 Claims, No Drawings

PESTICIDALLY ACTIVE PYRIMIDIN-5-YL-(THIO)PHOSPHORIC ACID ESTER-AMIDES

The invention relates to new substituted pyrimidin-5-yl-(thio)phosphoric acid ester-amides, several processes for their preparation and their use as agents for combating pests, in particular as arthropodicides, nematicides and fungicides.

It is known that certain thiophosphoric acid ester-amides, such as, for example, O-ethyl-O-(2-methyl-pyrimidin-5-yl)-N-methyl-, O-ethyl-O-(2-methyl-pyrimidin-5-yl)-N-i-propyl- and O-ethyl-O-(2-i-propyl-pyrimidin-5-yl)-N-i-propyl-thiophosphoric acid ester-amide, have an insecticidal action (compare DE-OS (German Published Specification) No. 2,643,262).

It is also known that certain bis-dithiocarbamates, such as, for example, zinc ethylene-bis-dithiocarbamate, have a fungicidal action (compare U.S. Pat. Nos. 2,457,764 and 3,050,439). However, the action of these compounds is not always completely satisfactory, especially when low amounts and concentrations are applied.

New substituted pyrimidin-5-yl-(thio)phosphoric acid ester-amides of the general formula (I)

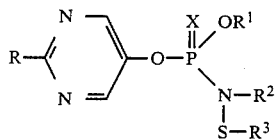

in which
X represents oxygen or sulphur,
R represents hydrogen, alkyl, aryl or cycloalkyl,
$R^1$ and $R^2$ are identical or different and represent alkyl and
$R^3$ represents alkyl, halogenoalkyl, cyanoalkyl, mono- or di-alkylamino, optionally substituted aryl or the groupings

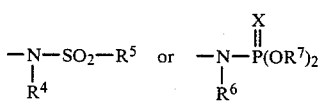

in which
X has the abovementioned meaning,
$R^4$, $R^6$ and $R^7$ are identical or different and represent alkyl and
$R^5$ represents alkyl or optionally substituted aryl,
have now been found.

It has furthermore been found that the new substituted pyrimidin-5-yl-(thio)phosphoric acid esteramides of the formula (I) are obtained by a process in which (a) phosphoric acid ester-amides of the general formula (II)

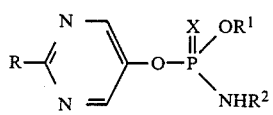

in which
X, R, $R^1$ and $R^2$ have the abovementioned meaning, are reacted with sulphenyl halides of the general formula (III)

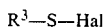

in which
$R^3$ has the abovementioned meaning and
Hal represents halogen, such as chlorine or bromine, if appropriate in the presence of an acid acceptor and if appropriate in the presence of a diluent, or (b) 5-hydroxypyrimidines of the general formula (IV)

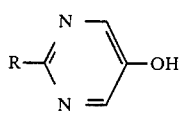

in which
R has the abovementioned meaning, or the corresponding alkali metal, alkaline earth metal or ammonium salts are reacted with sulphenylated phosphoric acid ester-amide halides of the general formula (V)

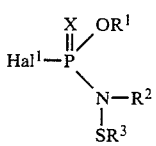

in which
X, $R^1$, $R^2$ and $R^3$ have the abovementioned meaning and
$Hal^1$ represents halogen, such as chlorine or bromine, if appropriate in the presence of an acid acceptor and if appropriate in the presence of a diluent.

The new substituted pyrimidin-5-yl-(thio)phosphoric acid ester-amides of the formula (I) are distinguished by a high activity as agents for combating pests, in particular by a high arthropodicidal (in particular insecticidal and acaricidal), nematicidal and fungicidal activity.

The alkyl radicals R, $R^1$, $R^2$, $R^3$, $R^4$, $R^5$, $R^6$ and $R^7$ and the alkyl parts of the halogenoalkyl, cyanoalkyl and mono- or di-alkylamino radicals $R^3$ can be branched or straight-chain and contain in each case 1 to 12, preferably in each case 1 to 8, in particular 1 to 6 and particularly preferably 1 to 4, carbon atoms. Halogenoalkyl preferably contains 1 to 5, in particular 1 to 3, identical or different halogen atoms, such as fluorine, chlorine, bromine and iodine, preferably fluorine and chlorine. Examples of these radicals which may be mentioned are: methyl, ethyl, n-propyl, i-propyl, n-butyl, i-butyl, sec.-butyl, tert.-butyl, n-pentyl, 1-methyl-butyl, 2-methyl-butyl, 3-methyl-butyl, 1,1-dimethyl-propyl, 2,2-dimethyl-propyl, 1,2-dimethyl-propyl and 1-ethyl-propyl, cyanomethyl, cyanoethyl, cyano-n-propyl, cyano-i-propyl, chloromethyl, chloroethyl, chloro-n-propyl, chloro-i-propyl, chlorodifluoromethyl, dichlorofluoromethyl, trifluoromethyl, trifluoroethyl, chlorodifluoroethyl, dichlorofluoroethyl, pentafluoro-n-propyl, (di)-methylamino, (di)-ethylamino, (di)-n-propylamino, (di)-i-propylamino, (di)-n-butylamino, (di)-i-butylamino, ethyl-methylamino, n-propyl-methylamino, i-propyl-methylamino, n-butyl-methylamino, i-butyl-methylamino, sec.-butyl-methylamino, tert.-butyl-methylamino, n-propylethylamino, i-propyl-ethylamino, n-butyl-ethylamino, i-butyl-ethylamino, sec.-butyl-ethylamino, tert.-butyl-ethylamino, i-propyl-n-propylamino, n-butyl-n-propylamino, i-butyl-n-propylamino, sec.-butyl-n-propylamino, tert.-butyl-n-propylamine, n-butyl-i-propylamino, i-butyl-i-propylamino, i-butyl-n-butylamino, sec.-butyl-n-butylamino or tert.-butyl-n-butylamino.

Aryl R and optionally substituted aryl $R^3$ and $R^5$ represents aryl with 6 to 10 carbon atoms, preferably optionally substituted phenyl or naphthyl, in particular optionally substituted phenyl.

Cycloalkyl R represents cycloalkyl with preferably 3 to 8, in particular 3 to 6, carbon atoms. Examples which may be mentioned are cyclopropyl, cyclobutyl, cyclopentyl and cyclohexyl.

The optionally substituted aryl radicals $R^3$ and $R^5$ can carry one or more, preferably 1 to 3 and in particular 1 or 2, identical or different substituents.

Examples of substituents which may be mentioned are: alkyl with preferably 1 to 4, in particular 1 or 2, carbon atoms, such as methyl, ethyl n- and i-propyl and n-, i-, s- and t-butyl; alkoxy with preferably 1 to 4, in particular 1 or 2, carbon atoms, such as methoxy, ethoxy, n- and i-propoxy and n-, i-, s- and t-butoxy; alkylthio with preferably 1 to 4, in particular 1 or 2, carbon atoms, such as methylthio, ethylthio, n- and i-propylthio and n-, i-, s- and t-butylthio; halogenoalkyl with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethyl; halogenoalkoxy with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethoxy, halogen, preferably fluorine, chlorine, bromine and iodine, in particular chlorine and bromine; and cyano and nitro.

Unless stated otherwise, halogen represents fluorine, chlorine, bromine or iodine, preferably fluorine or chlorine, it being possible for the halogen atoms to be identical or different.

The invention preferably relates to compounds of the general formula (I) in which X represents oxygen or sulphur (preferably sulphur),
R represents hydrogen, alkyl with 1 to 6 carbon atoms, aryl with 6 to 10 carbon atoms (preferably phenyl) or cycloalkyl with 3 to 6 carbon atoms,
$R^1$ and $R^2$ are identical or different and represent alkyl with 1 to 6 carbon atoms and
$R^3$ represents alkyl, halogenoalkyl, cycloalkyl, mono- or di-alkylamino with in each case 1 to 6 carbon atoms per alkyl part, an aryl radical which has 6 to 10 carbon atoms (preferably phenyl) and can be substituted by one or more (preferably 1 to 3, in particular 1 or 2) identical or different substituents from the series comprising halogen (such as fluorine, chlorine or bromine), cyano, nitro, halogenoalkyl and/or halogenoalkoxy with 1 to 6 carbon atoms and 1 to 5 identical or different halogen atoms (such as fluorine, chlorine or bromine) and/or alkyl with 1 to 4 carbon atoms, or the groupings

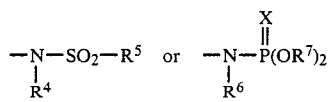

in which
X has the abovementioned meaning,
$R^4$, $R^6$ and $R^7$ are identical or different and represent alkyl with 1 to 6 carbon atoms, and
$R^5$ represents alkyl with 1 to 6 carbon atoms, or an aryl radical which has 6 to 10 carbon atoms (preferably phenyl) and can be substituted by one or more (preferably 1 to 3, in particular 1 or 2) identical or different substituents from the series comprising halogen (such as fluorine, chlorine or bromine), cyano, nitro, halogenoalkyl and/or halogenoalkoxy with 1 to 6 carbon atoms and 1 to 5 identical or different halogen atoms (such as fluorine, chlorine or bromine) and/or alkyl with 1 to 4 carbon atoms.

Particularly preferred compounds of the general formula (I) are those in which

X represents oxygen or sulphur (preferably sulphur),
R represents hydrogen, alkyl with 1 to 4 carbon atoms, phenyl or cycloalkyl with 3 to 6 carbon atoms,
$R^1$ and $R^2$ are identical or different and represent alkyl with 1 to 4 carbon atoms or n-pentyl, 1-methyl-butyl, 2-methyl-butyl, 3-methyl-butyl, 1,1-dimethyl-propyl, 2,2-dimethyl-propyl, 1,2-dimethyl-propyl or 1-ethyl-propyl and
$R^3$ represents alkyl with 1 to 4 carbon atoms, cyanoalkyl with 1 to 4 carbon atoms, halogenoalkyl with 1 to 4 carbon atoms and 1 to 5 halogen atoms, mono- or di-alkylamino with 1 to 4 carbon atoms per alkyl group, or phenyl, which can be substituted by one or two identical or different substituents from the series comprising halogen, cyano, nitro, alkyl with 1 to 4 carbon atoms, halogenoalkyl with 1 to 4 carbon atoms and 1 to 3 halogen atoms and/or halogenoalkoxy with 1 to 4 carbon atoms and 1 to 3 halogen atoms, or the groupings

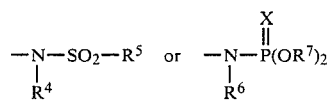

in which
X has the abovementioned meaning,
$R^4$, $R^6$ and $R^7$ are identical or different and represent alkyl with 1 to 4 carbon atoms and
$R^5$ represents alkyl with 1 to 4 carbon atoms, or phenyl, which can be substituted by one or two identical or different substituents from the series comprising halogen, cyano, nitro, alkyl with 1 to 4 carbon atoms, halogenoalkyl with 1 to 4 carbon atoms and 1 to 3 halogen atoms and/or halogenoalkoxy with 1 to 4 carbon atoms and 1 to 3 halogen atoms.

Very particularly preferred compounds of the general formula (I) are those in which X represents oxygen or sulphur (preferably sulphur),
R represents hydrogen, methyl, ethyl, n-propyl, i-propyl, n-butyl, i-butyl, sec.-butyl, tert.-butyl, phenyl, cyclopropyl or cyclohexyl, $R^1$ and $R^2$ are identical or different and represent methyl, ethyl, n-propyl, i-propyl, n-butyl, i-butyl, sec.-butyl, tert.-butyl, n-pentyl, 1-methyl-butyl, 2-methyl-butyl, 3-methyl-butyl, 1,1-dimethyl-propyl, 1,2-dimethyl-propyl, 2,2-dimethyl-propyl or 1-ethyl-propyl and $R^3$ represents methyl, ethyl, n-propyl, i-propyl, n-butyl, i-butyl, sec.-butyl, tert.-butyl, cyano-n-propyl, cyano-i-propyl, chloromethyl, chloroethyl, dichlorofluoromethyl, di-(n)-propylamino, di-(i)-propylamino, di-(n)-butylamino, phenyl, chlorophenyl, methylphenyl, chloro-trifluoromethyl-phenyl or the groupings

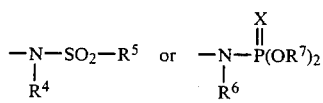

in which

X has the abovementioned meaning, $R^4$, $R^6$ and $R^7$ are identical or different and represent methyl, ethyl, n-propyl and/or i-propyl and $R^5$ represents methyl, phenyl and methylphenyl.

Of the compounds of the general formula (I), the compounds in which X represents sulphur are distinguished by particularly advantageous properties.

If, for example, O-ethyl-O-(2-methyl-pyrimidin-5-yl)-N-methyl-thiophosphoric cid ester-amide and dichlorofluoromethane-sulphenyl chloride are used as starting substances for process variant (a) according to the invention, the corresponding reaction can be outlined by the following equation:

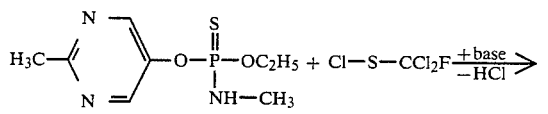

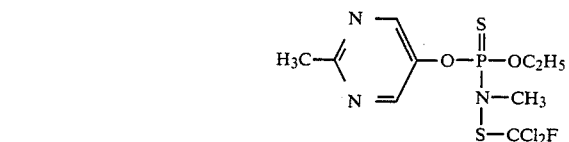

If, for example, 2-cyclopropyl-5-hydroxy-pyrimidine and O-ethyl-N-methyl-N-phenylthio-thiophosphoric acid ester-amide chloride are used as starting substances for process variant (b) according to the invention, the corresponding reaction can be outlined by the following equation:

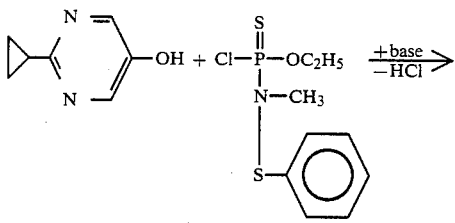

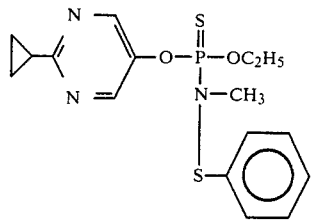

Formula (II) provides a definition of the phosphoric acid ester-amides to be used in process variant (a) according to the invention as starting substances for the preparation of the new compounds of the formula (I). In formula (II), X, R, $R^1$ and $R^2$ represent those radicals which have been mentioned above in the definition for formula (I).

Compounds of the formula (II) are known and can be prepared by generally known processes and methods (compare, for example, DE-OS (German Published Specification) No. 2,643,262, DE-OS (German Published Specification) No. 2,706,127 and DE-OS (German Published Specification) No. 2,835,492).

Formula (III) provides a definition of the sulphenyl halides also to be used as starting substances in process variant (a). In this formula, $R^3$ represents those radicals which have been mentioned above in the definition for formula (I). Hal in formula (III) represents halogen, such as, in particular, chlorine or bromine.

Compounds of the formula (III) are known and can be prepared by generally known methods (compare, for example, Methoden der organischen Chemie (Methods of Organic Chemistry), (Houben-Weyl-Müller) Thieme Verlag Stuttgart, 4th edition, Volume 9, page 268 et seq.).

Formula (IV) provides a definition of the 5-hydroxypyrimidines and the corresponding alkali metal, alkaline earth metal or ammonium salts to be used as starting substances in process variant (b). In this formula, R represents those radicals which have been mentioned above in the definition for formula (I). Preferred alkali metal and alkaline earth metal salts are the lithium, potassium, sodium and calcium salts, in particular the potassium, sodium and calcium salts.

Compounds of the formula (IV) are known and can be prepared by generally known processes and methods (compare, for example, DE-OS (German Published Specification) No. 2,643,262, DE-OS (German Published Specification) No. 2,706,127, DE-OS (German Published Specification) No. 2,835,492 and J. Chem. Soc., 1960, 4590).

Formula (V) provides a definition of the sulphenylated phosphoric acid ester-amide halides also to be used as starting substances in process variant (b). In this formula, X, $R^1$, $R^2$ and $R^3$ represent those radicals which have been mentioned in the definition for formula (I). $Hal^1$ in formula (V) represents halogen, in particular chlorine or bromine.

The compounds of the formula (V) can be prepared by customary methods, for example by reacting phosphoric acid amide halides with sulphenyl halides of the formula (III) in the presence of water-immiscible organic diluents, such as, for example, toluene, and if appropriate in the presence of acid acceptors, such as, for example, triethylamine, at temperatures between $-20°$ C. and $+40°$ C.

Process variants (a) and (b), according to the invention, for the preparation of the new substituted pyrimidin-5-yl-(thio)-phosphoric acid ester-amides of the formula (I) are preferably carried out using diluents. Possible diluents are virtually all the inert organic solvents.

These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylenesulphone and hexamethylphosphoric acid triamide.

If appropriate, the processes can be carried out in the presence of acid acceptors. All the customary acid-binding agents can be used as acid acceptors. Alkali metal carbonates and alcoholates, such as sodium carbonate and potassium carbonate, sodium methylate or ethylate and potassium methylate or ethylate, alkali metal hydrides, such as sodium hydride, and furthermore aliphatic, aromatic or heterocyclic amines, for example triethylamine, trimethylamine, dimethylaniline, dimethylbenzylamine and pyridine, have proved particularly suitable.

Process (a) according to the invention is in general carried out at temperatures between −20° C. and +60° C. The range between −10° C. and +40° C. is preferred. The reactions are in general carried out under normal pressure.

For carrying out process (a) according to the invention, the starting substances are usually employed in equimolar amounts. An excess of one or other of the reaction components provides no substantial advantages. The reaction is in general carried out in a suitable diluent in the presence of an acid acceptor and the reaction mixture is stirred at the required temperature. An organic solvent, for examwple toluene, is then added and the organic phase is worked up in the customary manner by washing, drying and distilling off the solvent.

Process (b) according to the invention is in general carried out at temperatures between 0° C. and 100° C. The range between 20° C. and 80° C. is preferred. The reactions are in general carried out under normal pressure.

The starting substances are usually employed in approximately equimolar amounts for carrying out process (b) according to the invention. An excess of one or the other of the reaction components provides no substantial advantages. The reaction is in general carried out in a suitable diluent in the presence of an acid acceptor, and the reaction mixture is stirred at the required temperature for several hours. An organic solvent, for example toluene, is then added and the organic phase is worked up in the customary manner by washing, drying and distilling off the solvent.

The new compounds are obtained in the form of oils, some of which cannot be distilled without decomposition, but which can be freed from the last volatile constituents by so-called "incipient distillation", that is to say by prolonged heating to moderately elevated temperatures under reduced pressure, and can be purified in this manner. They are characterized by their refractive index.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera spec.* From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex Lectularius, Rhodnius prolixus* and Triatoma spp. From the order of Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma Lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata Lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malaco soma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anoibium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp, Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinea, Eriophyes ribis, Phyllocoptruta oleivora,* Boophilus spp., Rhipicephalus spp., Amblyomma spp., Hyalomma spp, Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compounds according to the invention also exhibit a powerful microbicidal action, in particular a fungicidal action, and can be employed in practice for combating undesired micro-organisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for systemic and protective combating of rice diseases, such as *Pyricularia oryzae.* Good actions are likewise achieved in combating Oomycetes.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

These formulations are produced in known manner, for example by mixing the active compounds with extenders, that is, liquid solvents, liquefied gases under pressure, and/or solid carriers, optionally with the use of surface-active agents, that is, emulsifying agents and/or foam-forming agents. In the case of the use of water as an extender, organic solvents can, for example, also be used as auxiliary solvents. As liquid solvents, there are suitable din the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable; for example lignin-sulphite waste liquors and methylcellulose.

Adhesive such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 05 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by micro-organisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Process variants (a) and (b) according to the invention are explained with reference to the following preparation examples:

EXAMPLE 1

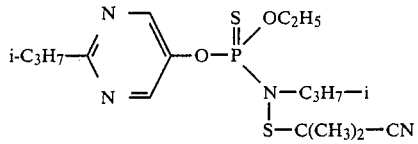

(Process variant a)

15.2 g (0.05 mole) of O-ethyl-O-(2-i-propylpyrimidin-5-yl)-N-i-propyl-thiophosphoric acid esteramide are added to a suspension of 2.3 g (0.075 mole) of 80% pure sodium hydride in 100 ml of tetrahydrofuran and the mixture is stirred at 50° C. to 60° C. for 0.5 hour. 6.8 g (0.05 mole) of 1-cyano-1-methyl-ethylsulphenyl chloride are then added dropwise at a temperature of 5° C. to 10° C. and the mixture is subsequently stirred at 20° C. for 1 hour. At 20° C. to 25° C., 10 ml of water are added dropwise and the mixture is diluted with 200 ml of toluene and extracted with two 50 ml portions of water. The organic phase is dried over sodium sulphate and evaporated under a waterpump vacuum. The residue is subjected to incipient distillation under a high vacuum.

16.2 g (81% of theory) of O-ethyl-O-(2-i-propylpyrimidin-5-yl)-N-(i-propyl)-N-(1-cyano-1-methylethylthio)-thiophosphoric acid ester-amide are obtained as a brown oil of refractive index $n_d^{20}$ 1.5183.

EXAMPLE 2

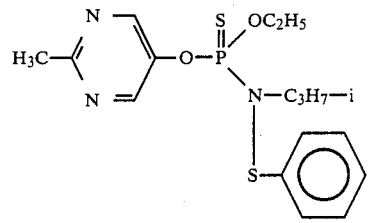

(Process variant b)

A mixture of 5.72 g (0.052 mole) of 5-hydroxy-2-methylpyrimidine, 10 g (0.075 mole) of potassium carbonate, 100 ml of acetonitrile and 15.5 g (0.05 mole) of O-ethyl-N-(i-propyl)-N-(phenylthio)-thiophosphoric acid ester-amide chloride is stirred at 40° C. for 2 hours. After addition of 200 ml of toluene, the mixture is extracted with two 30 ml portions of water, the organic phase is dried over sodium sulphate and the solvent is removed under a waterpump vacuum. The residue is distilled under a high vacuum.

17 g (89% of theory) of O-ethyl-O-(2-methylpyrimidin-5-yl)-N-(i-propyl)-N-(phenylthio)-thiophosphoric acid ester-amide are obtained in this manner in the form of a yellow oil of refractive index $n_D^{21}$ 1.5709.

The following compounds of the formula (I) are obtained analogously to Example (1) and (2) or process variant (a) and (b):

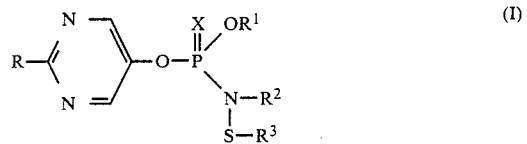

TABLE 1

| Example No. | R | R¹ | R² | R³ | X | Refractive index |
|---|---|---|---|---|---|---|
| 3 | $C_3H_7$—iso | $C_2H_5$ | $C_3H_7$—iso | N(CH₃)(PO(OC₂H₅)₂) | S | $n_D^{26}$: 1.5028 |
| 4 | $CH_3$ | $C_2H_5$ | $C_3H_7$—iso | phenyl | O | $n_D^{26}$: 1.5471 |
| 5 | $CH_3$ | $C_2H_5$ | $CH_3$ | phenyl | S | $n_D^{26}$: 1.5780 |
| 6 | $CH_3$ | $C_2H_5$ | $CH_3$ | $C(CH_3)_2CN$ | S | $n_D^{26}$: 1.5312 |
| 7 | $CH_3$ | $C_2H_5$ | $CH_3$ | $CCl_2F$ | S | $n_D^{20}$: 1.5382 |

TABLE 1-continued

| Example No. | R | R¹ | R² | R³ | X | Refractive index |
|---|---|---|---|---|---|---|
| 8 | $CH_3$ | $C_2H_5$ | $CH_3$ | 2-CF₃, 4-Cl-phenyl | S | $n_D^{20}$: 1.5522 |
| 9 | $C_4H_9$—tert. | $C_2H_5$ | $C_2H_5$ | phenyl | S | $N_D^{20}$: 1.5591 |
| 10 | $C_4H_9$—tert. | $C_2H_5$ | $C_2H_5$ | $CCl_2F$ | S | $n_D^{20}$: 1.5210 |
| 11 | $C_4H_9$—tert. | $C_2H_5$ | $C_2H_5$ | $CH_2$—$CH_2Cl$ | S | $n_D^{20}$: 1.5271 |
| 12 | phenyl | $C_2H_5$ | $C_3H_7$—iso | phenyl | S | |
| 13 | $C_4H_9$—tert. | $CH_3$ | $C_2H_5$ | phenyl | S | |
| 14 | $C_4H_9$—tert. | $C_3H_7$—iso | $C_2H_5$ | phenyl | S | |
| 15 | $C_2H_5$ | $C_2H_5$ | $C_2H_5$ | $C(CH_3)_2CN$ | S | |
| 16 | cyclopropyl | $C_2H_5$ | $C_2H_5$ | $C_4H_9$—tert. | S | |
| 17 | cyclohexyl | $C_2H_5$ | $C_3H_7$—iso | phenyl | S | |
| 18 | $C_4H_9$—tert. | $C_2H_5$ | $C_2H_5$ | N(CH₃)SO₂-4-CH₃-phenyl | S | |
| 19 | $C_3H_7$—iso | $CH_3$ | $CH_3$ | phenyl | S | |
| 20 | $C_4H_9$—tert. | $C_3H_7$—iso | $C_3H_7$—iso | $CCl_2F$ | S | |
| 21 | $C_4H_9$—tert. | $C_2H_5$ | $C_2H_5$ | $N(C_4H_9-n)_2$ | S | |

The sulphenylated phosphoric acid ester-amide halides of the formula (V) to be used as starting substances are prepared as follows:

Example a

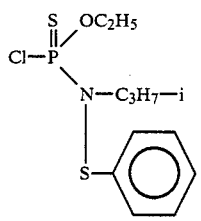

First 16 g (0.11 mole) of phenylsulphenyl chloride and then 12 g (0.12 mole) of triethylamine are added dropwise to a solution of 20.2 g (0.1 mole) of O-ethyl-N-i-propyl-thiophosphoric acid ester-amide chloride in 100 ml of toluene at 0° C. to 10° C.

The mixture is subsequently stirred at 20° C. for 1 hour, 100 ml of toluene are then added and the mixture is extracted with two 30 ml portions of water. The organic phase is dried over sodium sulphate and concentrated under a waterpump vacuum. The residue is rectified.

22 g (71% of theory) of O-ethyl-N-(i-propyl)-N-(phenylthio)-thiophosphoric acid ester-amide chloride are obtained in this manner in the form of a yellow oil.

Boiling point: 142° C./26.7 Pa (0.2 mm Hg).

The remaining starting substances of the formula (V) are obtained analogously to Example (a).

The biological activity of the compounds of the general formula (I) may be illustrated with the aid of the following examples:

EXAMPLE A

Tetranychus test (resistant)
Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (Tetranychus urticae) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, for example the compounds from preparation examples: (1), (2), (5) and (6) exhibited a destruction of 100% after 2 days, at an active compound concentration of 0.1%.

EXAMPLE B

Phaedon larvae test
Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (Phaedon cochleariae), as long as the leaves are still moist.

After the specified periods of time, the destruction in % is determined. 100% means that all the beatle larvae have been killed; 0% means that none of the beatle larvae have been killed.

In this test, for example, the compounds from preparation examples (8), (9) and (10) exhibited a destruction of 100% after 3 days, at an active compound concentration of 0.01%.

EXAMPLE C

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, lettuce is sown in and the pots are kept at a greenhouse temperature of 27° C.

After four weeks, the lettuce roots are examined for infestation with nematodes (root galls), and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compounds of preparation examples (1), (2), (3), (5), (6) and (11) exhibited a destruction of 100%, at an active compound concentration of 20 ppm.

EXAMPLE D

Test insect: *Phaedon cochleariae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all the test insects have been killed and 0% if just as many test insects are still alive as in the case of the untreated control.

In this test, for example, the compounds from preparation examples (4), (5) and (6) exhibited a destruction of 100%, at an active compound cincentration of 20 ppm.

EXAMPLE E

Test insect: *Myzus Persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all the test insects have been killed and 0% if just as many test insects are still alive as in the case of the untreated control.

In this test, for example, the compounds from preparation examples (2), (4), (5), (6), (7) and (8) exhibited a destruction of 100%, at an active compound concentration of 20 ppm.

EXAMPLE F

Test insects: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of the active compound is intimately mixed with soil. The concentration of the active compound in the preparation is of practically no importance, only the amount by weight of active compound per unit volume of soil, which is given in ppm (=mg/l) being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of preparation examples (1), (9) and (10) exhibited a desruction of 100%, at an active compond concentration of 20 ppm.

EXAMPLE G

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, for example, the compounds according to the following preparation examples exhibited a very good activity: (2), (5) and (6).

EXAMPLE H

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the state amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, for example, the compounds according to the following preparation examples exhibited a good activity, (2) and (5).

It is understood that the specification and examples are illustrative but not limitative of the present invention and that other embodiments within the spirit and scope of the invention will suggest themselves to those skilled in the art.

We claim:

1. A pyrimidin-5-yl-(thio)phosphoric acid esteramide of the formula $$R-\underset{N}{\overset{N}{\underset{\parallel}{\bigg\langle}}}-O-\overset{X}{\underset{\parallel}{P}}\overset{OR^1}{\underset{\underset{S-R^3}{|}}{\diagdown N-R^2}}$$

in which
X is oxygen or sulphur,
R is hydrogen, alkyl with 1 to 6 carbon atoms, aryl with 6 to 10 carbon atoms, or cycloalkyl with 3 to 6 carbon atoms,
$R^1$, $R^2$, $R^4$, $R^6$ and $R^7$ each independently is alkyl with 1 to 6 carbon atoms,
$R^3$ is alkyl, halogenoalkyl, cyanoalkyl, mono- or di-alkylamino with in each case 1 to 6 carbon atoms per alkyl part, an aryl radical which has 6 to 10 carbon atoms and is optionally substituted by at least one substituent independently selected from halogen, cyano, nitro, halogenoalkyl and halogenoalkoxy with 1 to 6 carbon atoms, and alkyl with 1 to 4 carbon atoms, or $$-\underset{R^4}{\overset{|}{N}}-SO_2-R^5 \quad \text{or} \quad -\underset{R^6}{\overset{|}{N}}-\overset{X}{\underset{\parallel}{P}}(OR^7)_2,$$

and
$R^5$ is alkyl with 1 to 6 carbon atoms, or an aryl which has 6 to 10 carbon atoms and optionally substituted by at least one substituent independently selected from halogen, cyano, nitro, halogenoalkyl and halogenoalkoxy with 1 to 6 carbon atoms and 1 to 5 halogen atoms, and alkyl with 1 to 4 carbon atoms.

2. A pyrimidin-5-yl-(thio)phosphoric acid ester-amide according to claim 1, in which R is hydrogen, alkyl with 1 to 4 carbon atoms, phenyl or cycloalkyl with 3 to 6 carbon atoms, $R^1$ and $R^2$ each independently is alkyl with 1 to 4 carbon atoms or n-pentyl, 1-methyl-butyl, 2-methyl-butyl, 3-methyl-butyl, 1,1-dimethyl-propyl, 2,2-dimethyl-propyl, 1,2-dimethyl-propyl or 1-ethyl-propyl, $R^3$ is alkyl with 1 to 4 carbon atoms, cyanoalkyl with 1 to 4 carbon atoms, halogenoalkyl with 1 to 4 carbon atoms and 1 to 5 halogen atoms, mono- or di-alkylamino with 1 to 4 carbon atoms per alkyl group, or phenyl which is optionally substituted by one or two identical or different substituents selected from halogen, cyano, nitro, alkyl with 1 to 4 carbon atoms, halogenoalkyl with 1 to 4 carbon atoms and 1 to 3 halogen atoms, halogenoalkoxy with 1 to 4 carbon atoms and 1 to 3 halogen atoms,

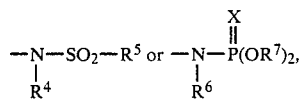

$R^4$, $R^6$ and $R^7$ each independently is alkyl with 1 to 4 carbon atoms, and $R^5$ is alkyl with 1 to 4 carbon atoms, or phenyl which is optionally substituted by one or two identical or different substituents selected from halogen, cyano, nitro, alkyl with 1 to 4 carbon atoms, halogenalkyl with 1 to 4 carbon atoms and 1 to 3 halogen atoms, and halogenoalkoxy with 1 to 4 carbon atoms and 1 to 3 halogen atoms.

3. A pyrimidin-5-yl-(thio)phosphoric acid ester-amide according to claim 1, in which R is hydrogen, methyl, ethyl, n-propyl, i-propyl, n-butyl, i-butyl, sec.-butyl, tert.-butyl, phenyl, cyclopropyl or cyclohexyl, $R^1$ and $R^2$ each independently is methyl, ethyl, n-propyl, i-propyl, n-butyl, i-butyl, sec.-butyl, tert.-butyl, n-pentyl, 1-methyl-butyl, 2-methyl-butyl, 3-methyl-butyl, 1,1-dimethyl-propyl, 1,2-dimethyl-propyl, 2,2-dimethyl-propyl or 1-ethyl-propyl, $R^3$ is methyl, ethyl, n-propyl, i-propyl, n-butyl, i-butyl, sec.-butyl, tert.-butyl, cyano-n-propyl, cyano-i-propyl, chloromethyl, chloroethyl, dichlorofluoromethyl, di-(n)-propylamino, di-(i)-propylamino, di-(n)-butylamino, phenyl, chlorophenyl, methylphenyl, chloro-trifluoromethyl-phenyl,

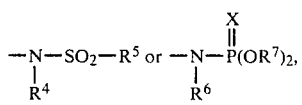

$R^4$, $R^6$ and $R^7$ each independently is methyl, ethyl, n-propyl or i-propyl, and $R^5$ is methyl, phenyl or methylphenyl.

4. A pyrimidin-5-yl-(thio)phosphoric acid ester amide according to claim 1, in which X is sulphur.

5. A compound according to claim 1, wherein such compound is O-ethyl-O-(2-i-propylpyrimidin-5-yl)-N-(i-propyl)-N-(1-cyano-1-methylethylthio)-thiophosphoric acid ester amide of the formula

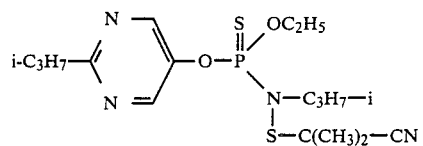

6. A compound according to claim 1, wherein such compound is O-ethyl-O-(2-methylpyrimidin-5-yl)-N-(i-propyl)-N-(phenylthio)-thiophosphoric acid ester-amide of the formula

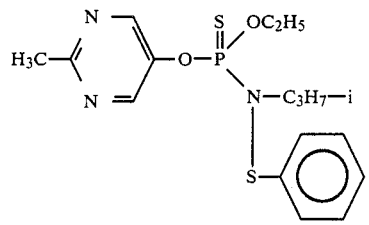

7. A compound according to claim 1, wherein such compound is O-ethyl-O-(2-isopropyl-pyrimidin-5-yl)-N-isopropyl-N-(N'-methyl-diethoxyphosphorylamidothio)-thiophosphoric acid ester-amide of the formula

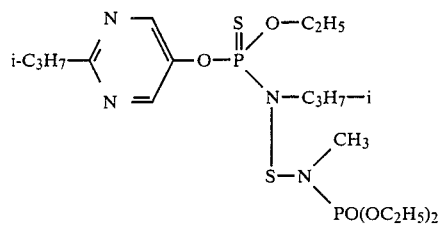

8. A compound according to claim 1, wherein such compound is O-ethyl-O-(2-methyl-pyrimidin-5-yl)-N-methyl-N-fluorodichloromethylthio-thiophosphoric acid ester-amide of the formula

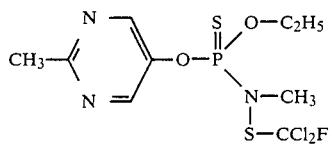

9. A compound according to claim 1, wherein such compound is O,N-diethyl-O-(2-tert.-butyl-pyrimidin-5-yl)-N-fluorodichloromethylthio-thiophosphoric acid ester-amide of the formula

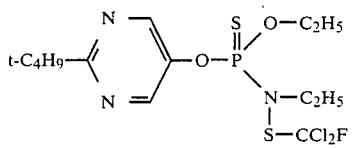

10. An arthropodicidal, nematocidal and fungicidal composition comprising an arthropodicidal, nematocidal and fungicidally effective amount of a compound according to claim 1 in admixture with a diluent.

11. A method of combatting arthropods, nematodes and fungi which comprises administering to such arthropods, nematodes or fungi or to a habitat thereof an arthropodicidally, nematocidally or fungicidally effective amount of a compound according to claim 1.

12. The method according to claim 11, wherein such compound is

O-ethyl-O-(2-i-propyl-pyrimidin-5-yl)-N-(i-propyl)-N-(1-cyano-1-methylethyl-thio)-thiophosphoric acid ester-amide, O-ethyl-O-(2-methyl-pyrimidin-5-yl)-N-(i-propyl)-N-(phenylthio)-thiophosphoric acid ester-amide, O-ethyl-O-(2-isopropyl-pyrimidin-5-yl)-N-isopropyl-N-(N'-methyl-diethoxyphosphorylamido-thio)thiophosphoric acid ester-amide, O-ethyl-O-(2-methyl-pyrimidin-5-yl)-N-methyl-N-fluorodichloromethylthio-thiophosphoric acid ester-amide or O-N-diethyl-O-(2-tert.-butyl-pyrimidin-5-yl)-N-fluorodichloromethylthio-thiophosphoric acid ester-amide.

* * * * *